United States Patent [19]

Briggs et al.

[11] Patent Number: 4,752,479

[45] Date of Patent: Jun. 21, 1988

[54] MULTI VITAMIN AND MINERAL DIETARY SUPPLEMENT WITH CONTROLLED RELEASE BIOAVAILABLE IRON

[75] Inventors: Ronald S. Briggs, Lebanon; Richard Braun, Colts Neck; Stephen Chen, East Brunswick, all of N.J.

[73] Assignee: Ciba-Geigy Corporaton, Ardsley, N.Y.

[21] Appl. No.: 866,841

[22] Filed: May 27, 1986

[51] Int. Cl.$^4$ .......................... A61K 9/22; A61K 9/24; A61K 33/26; A61K 33/06

[52] U.S. Cl. .................................... 424/472; 424/468; 424/471; 424/469; 424/147; 424/154; 424/156

[58] Field of Search ............... 424/147, 141, 621, 472, 424/471, 469, 476, 498, 502; 514/474

[56] References Cited

U.S. PATENT DOCUMENTS

| | | | |
|---|---|---|---|
| Re. 27,107 | 3/1971 | Levesque | 424/22 |
| 2,811,483 | 10/1957 | Aterno et al. | 514/474 |
| 3,035,985 | 5/1962 | Stoyle et al. | 424/147 |
| 3,081,233 | 3/1963 | Enz et al. | 167/82 |
| 3,125,491 | 3/1964 | Elowe et al. | 514/474 |
| 3,384,546 | 5/1968 | Palermo | 514/474 |
| 3,446,899 | 5/1969 | Cavalli et al. | 514/474 |
| 3,458,623 | 7/1969 | Raymond et al. | 424/147 |
| 3,584,114 | 6/1971 | Cavalli et al. | 424/147 |
| 3,829,561 | 8/1974 | Heinrich | 424/44 |
| 3,860,733 | 1/1975 | Morse et al. | 424/35 |
| 4,327,076 | 4/1982 | Puglia et al. | 424/147 |
| 4,327,077 | 4/1982 | Puglia et al. | 424/147 |
| 4,431,634 | 2/1984 | Ellenbogen | 424/147 |
| 4,495,177 | 1/1985 | Taracatac et al. | 424/147 |

FOREIGN PATENT DOCUMENTS

| | | |
|---|---|---|
| 0013131 | 7/1980 | European Pat. Off. . |
| 267221 | 3/1950 | Switzerland . |
| 1302266 | 1/1973 | United Kingdom . |
| 2121277 | 12/1983 | United Kingdom . |
| 2123690 | 2/1984 | United Kingdom . |

OTHER PUBLICATIONS

Little et al., Tablet Making 2nd Ed. (1963) Northern Pub. Co., Liverpool, England, pp. 6–16, 61–68, 107–111, 121.
Opadry Product Literature.
Dorland's Illustrated Medical Dictionary, 25 Ed., p. 200, W. B. Saunders (Philadelphia 1965).

*Primary Examiner*—Shep K. Rose
*Attorney, Agent, or Firm*—Irving M. Fishman

[57] ABSTRACT

A multi vitamin and mineral dietary supplement composition for oral administration containing, per unit dose,
(a) one or more divalent dietary mineral components selected from the group consisting of bioavailable calcium and magnesium, and in the further presence or absence of one or more additional non-ferrous mineral and vitamin components, adapted to be released in the upper gastrointestinal tract, and
(b) a bioavailable iron component, present in controlled release form, so adapted so as to be subsequently released in a controlled manner lower in the gastrointestinal tract, and a method of preventing or treating iron deficiency using such compositions.

13 Claims, No Drawings

MULTI VITAMIN AND MINERAL DIETARY SUPPLEMENT WITH CONTROLLED RELEASE BIOAVAILABLE IRON

BACKGROUND OF THE INVENTION

Iron containing vitamin and mineral supplement preparations for oral administration are generally used to supplement an individual's diet to prevent or treat iron deficiency. Often, when a single dietary mineral deficiency occurs, other nutritional deficiencies are likely to ensue. For example, in iron deficiency anemia due to inadequacy in the diet, the likelihood exists that the diet is also low in other basic requirements. Such multiple deficiencies are apt to occur in times of increased growth or stress, as in pregnancy and lactation, when nutritional needs are high. Such deficiencies are also likely to occur in individuals whose diets are inadequate due to diet restrictions and personal idiosyncracies, and in individuals suffering from conditions known to adversely affect the absorption, utilization or excretion of essential minerals, such as iron.

Unfortunately, the absorption of iron supplements from the gastrointestinal tract is reduced in the presence of divalent non-iron mineral supplements such as magnesium, and calcium. See Goodman et al., the Pharmacological Basis of Therapeutics, Third Edition, page 1396 (1968), Freeman et al., Am. J. Physiol., 137, p. 706–9 (1942), and Amine et al., N. Nutrition, 101, p. 927–936 (1971). Many prenatal iron supplement compositions described in the literature accordingly contain limited quantities of calcium and/or magnesium, eg. Filibon ® prenatal capsules, PDR 20th Ed., p. 670 (1965) and U.S. Pat. No. 4,431,634.

Moreover, iron containing dietary preparations can induce constipation diarrhea, and abdominal discomfort. As a result, iron supplement preparations have been formulated in sustained release waxy matrix form, e.g. Slow Fe ®. It has also been proposed to incorporate multicomponent dietary supplements in a porous plastic matrix in order to release such supplments into the gastro-intestinal tract over a period of time, as see for example, U.S. Pat. No. Re. 27,107. While the formulation of iron containing multi-mineral component compositions in slow release form may reduce constipation diarrhea, and associated gastro-intestinal disturbances, the reduction of iron availability to the host due to the simultaneous release of iron, magnesium and calcium in such preparations substantially limits the desired beneficial effect.

It is an object of the present invention to obviate the deficiencies of prior multimineral preparations by providing compositions that enable the host to absorb the iron and divalent mineral components with maximum efficiency and with reduced gastrointestinal side effects.

It is a further object of the present invention to provide a method of preventing or treating iron deficiency in a host by administering to the host an effective multimineral dietary amount of such compositions.

These and other objects of the instant invention are apparent from the following disclosures.

DETAILED DESCRIPTION OF THE INVENTION

One embodiment of the invention relates to a multimineral dietary supplemental composition for oral administration containing, per unit dose (a) one or more divalent dietary mineral components selected from the group consisting of bioavailable calcium and magnesium, and (b) a bioavailable iron component, present in controlled release form, so adapted so as to be subsequently released in a controlled continuous manner lower in the gastrointestinal tract.

Advantageously, such compositions can be formulated by providing unit dose formulations containing an outer layer containing the divalent mineral components, (a) and an inner core containing the bioavailable iron component in controlled release form, (b). Surrounding the outer layer, one may optionally provide a protective coating or film, for stability, cosmetic or palatability purposes. Further, if desired, the between inner core and the outer layer there may be interposed a protective coating or layer, for example to maintain integrety of the inner core and outer layer and obviate the possibility of any substantial migration of ingredients, eg. during storage, between the inner core and the outer layer of active ingredients.

By virtue of its release into the upper gastrointestinal tract, the calcium and/or magnesium component can be substantially absorbed into the body of the host prior to the controlled continuous release of the bioavailable iron component lower in the gastrointestinal tract. In this manner, the interfering effect of calcium and magnesium upon the absorption of iron is minimized. As a result, the body's utilization of these mineral components can be effectively maximized. Furthermore, the presence of excessively large amounts of iron component, which may otherwise have been needed to achieve the desired level of absorption due to the interfering effects of the divalent calcium and magnesium components, can be obviated. This is especially advantageous since relatively large amounts of iron can induce undesired side effects, such as constipation.

Within the context of the instant disclosure, the upper gastrointestinal tract includes the stomach and the upper duodenum. Preferably, the bioavailable calcium and/or magnesium, as well as any additional non-ferrous mineral and vitamin components, are released into the stomach and upper duodenum and subsequently the iron supplement component is released. Advantageously the iron is subsequently released primarily in the duodenum and jejunum in a controlled continuous manner to maximize host toleration and absorption.

Dietary calcium includes those calcium compounds conventionally employed in oral supplement formulations, such as bone meal, oyster shell, calcium carbonate, calcium sulfate, calcium gluconate, calcium lactate, calcium phosphate, including dibasic calcium phosphate and tribasic calcium phosphate, and calcium levulinate. Preferred is calcium carbonate or sulfate. Dietary magnesium likewise includes those magnesium compounds conventionally employed in oral supplement formulations, such as magnesium carbonate, magnesium oxide, magnesium hydroxide and magnesium sulfate. Preferred is magnesium oxide.

As the bioavailable iron component, there may be employed conventional ferrous oral dietary supplements including, for example, ferrous sulfate, ferrous fumarate, ferrous gluconate, ferrous succinate, ferrous glutamate, ferrous lactate, ferrous citrate, ferrous tartrate, ferrous pyrophosphate, ferrus cholinisocitrate and ferrous carbonate. Preferred is ferrous sulfate.

The multimineral compositions may also contain other mineral components in amounts conventionally employed in oral dietary supplements including: copper, for example in the form of cupric oxide, cupric sulfate or cupric gluconate; phosphorous, for example in the form of calcium phosphate or bone meal; iodine, for example in the form of sodium or potassium iodide; zinc, for example in the form of zinc chloride, zinc sulfate or zinc oxide; chromium, for example as chromic chloride; molybdenum, for example as sodium molybdate; selenium, for example as sodium selenate; and manganese, for example as manganese sulfate or chloride.

The inner core, containing the bioavailable iron component, may be in the form of a tablet or as a collection of pellets or granules contained within a water soluble capsule, which tablet or capsule containing granules is designed to release the iron component in a continuous manner. In general, the core advantageously releases the iron component in the gastrointestinal tract over a period between about 2 and about 8 hours. Such tablets and encapsulated pellets or granules can be prepared by methods known in the art.

For example, granulates of ferrous sulfate, fumarate, gluconate, succinate, glutamate, lactate or the like, may be mixed with a coating solution containing a plastic or waxy film former, advantageously in the presence of an inert volatile diluent, such as methanol, ethanol or methylene chloride, to coat the ferrous granulates, followed by evaporation of the volatile diluent and compression of the coated granulates to form a tablet containing the ferrous salt within the plastic or waxy matrix. Preferred plastic or waxy film formers are those that will absorb aqueous gastrointestinal fluid and release the ferrous component by gradual dissolution or through osmotically generated passages and the like. Suitable plastic or waxy film formers include: cellulose ethers, such as ethyl cellulose, ethyl hydroxyethylcellulose, and hydroxypropyl methylcellulose; cellulose esters such as cellulose acetate, cellulose acetate phthalate, and cellulose nitrate; acrylate and methacrylate polymers; polyamide resins; alkyd resins, such as phthalic anhydride-polyhydric alcohol-oil combinations; urethanes; and shellac. Preferred are cellulose ethers and esters. Release rate modifying agents, such as sugars, castor oil, hydrogenated oils, higher fatty alcohols, higher fatty acids, polyethylene glycol, polypropylene glycol and the like, and mixtures thereof, may also be incorporated with the iron granulate.

Alternatively, the ferrous component may be incorporated in water-swellable coated granules or beads contained within a water soluble capsule, such as a gelatin capsule, prepared for example according to the process disclosed in U.S. Pat. No. 3,247,066.

The loaded ferrous component containing pellet can then be used as the core of the multimineral dietary supplement.

The divalent mineral component containing outer layer may contain, as stated above, other mineral components. Also, in a preferred embodiment of the invention, the outer layer may also contain conventional vitamin components, most preferably in sufficient amounts such that the total daily dose contains the United States recommended daily allowance (U.S. RDA) of one or more of such vitamin components for adults. Conventional vitamin components include vitamin A (eg. as the acetate or palmitate), vitamin D (eg. as cholecalciferol), vitamin $B_1$ (eg. as thiamine mononitrate), vitamin $B_2$ (eg. as riboflavin), vitamin $B_6$ (eg. as pyridoxine hydrochloride), vitamin $B_{12}$ (eg. as cyanocobalamin), vitamin C (eg. as ascorbic acid or sodium ascorbate), vitamin D, vitamin E (eg. as the dl-alpha tocopheryl acetate), folic acid and niacin (eg. as niacinamide). Optionally, additional vitamins, such as vitamin $K_1$ (eg. as phytonadione), biotin, and pantothenic acid (eg. as calcium pantothenate) may also be incorporated into the divalent mineral component containing outer layer, in amounts such that the total daily dose contains up to the U.S. RDA of such components, or in the case of vitamin $K_1$, up to about 100 mg per total daily dose.

The components of the outer layer are characteristically blended with conventional excipients such as binders, including gelatin, pregelatinized starch and the like; lubricants, such as hydrogenated vegetable oil, stearic acid, and the like; diluents, such as lactose, mannose or sucrose; disintegrants, such as carboxymethyl cellulose or sodium starch glycolate; suspending agents, such as povidone, polyvinylalcohol and the like; and absorbents, such as silicon dioxide.

The unit dose preparation, incorporating the inner core containing the ferrous component, and the outer layer, containing the divalent dietary mineral components and optionally the aforementioned non-ferrous mineral and/or vitamin components are combined in the form of a unit dose preparation, advantageously as a tablet, by methods known, per se, in the art. For example, the inner core, containing the controlled release ferrous component, can be placed within a tablet die containing a portion of the outer layer component in partially compressed form having a cavity within which the core is placed, and subsequently the remaining portion of outer layer component is added in granulated form, and the total die components are then fully compressed.

Subsequently, a film coating may be added to protect the ingredients from moisture, oxygen or light and to mask unpleasant taste or appearance. Suitable tablet coating agents include cellulose acetate phthalate, gelatin, hydroxypropyl cellulose, hydroxypropylmethyl cellulose, cellulose phthalate, methacrylic copolymer and shellac. An enteric coating may be employed, as well as coloring agents for identification, and if desired, the tablet may be polished with a waxy composition, such as carnuba wax.

In a preferred embodiment, the total daily dosage is in the form of one or two tablets, most preferably two tablets, each having a tablet weight between about 600 to about 1200 mg. Where two tablets are employed, each preferably contains at least 50 weight percent of the U.S. RDA of iron, eg. between about 15 and 60 mg iron, more preferably between 20 and 40 mg iron. Preferred amounts of divalent calcium, eg. as calcium carbonate, sulfate, gluconate, phosphate or the like, are between about 50 and about 200 mg per tablet, more preferably between about 75 and about 150 mg per tablet. Preferred amounts of magnesium are between about 5 and 50 mg, preferably between about 8 and about 20 mg, per tablet, for example as magnesium carbonate, oxide, hydroxide or sulfate.

The following example is for illustrative purposes and is not be be construed as limiting the invention. All parts are by weight unless otherwise specified.

EXAMPLE 1

To 96.0 parts of ferrous sulfate, there is added 75.9 parts lactose, 5.4 parts hydroxypropylmethyl cellulose and 0.9 parts cetostearyl alcohol in the presence of 30 parts methylene chloride and the ingredients are mixed thoroughtly, dried, and granulated in a granulator fitted with a 1.5 mm sieve. The granulate is then mixed with 3.6 parts magnesium stearate. The resulting granulates are then compressed into tablets having an individual weight of about 181.8 mg and thin film coated with a mixture of 21 parts of a commercial film coating agent, Opadry ® (Hydroxypropyl Methylcellulose/polyethylene glycol) light orange formulation by Colorcon, dissolved in a solution of 251 parts methylene chloride and 151 parts methanol, and are thoroughly dried to form the ferrous core component having a weight of 202.8 mg and containing 96 mg ferrous sulfate (equivalent to 30 mg bioavailable iron).

In a second blending operation, the following ingredients are combined in parts by weight: calcium sulfate, 343 parts; copper oxide 1.38 parts; zinc sulfate, 37.8 parts; magnesium oxide, 22.8 parts; potassium iodide, 0.216 parts and povidone, 8 parts; and to this mixture there is added approximately 1.2 parts water and 25 parts methanol and the mixture granulated, dried and milled to form a milled mineral granulate. To this milled mineral granulate there is added: ascorbic acid, 66 parts; vitamin A acetate/vitamin D blend having a ratio of 500 IU to 50 IU, 10.8 parts; vitamin E as dl-alpha tocopherylacetate, 33 parts; niacinamide, 11 parts; riboflavin, 1.88 parts; thiamine mononitrate, 1.728 parts; pyridoxine hydrochloride, 2.2 parts; folic acid, 0.63 parts; vitamin $B_{12}$ (19% S.D.), 0.75 parts; in the presence of lactose, 65.2 parts; starch, 42.5 parts; silicon dioxide, 3.4 parts; hydrogenated vegetable oil, 50 parts; and sodium starch glycolate, 29.2 parts. While blending the aforementioned ingredients, there is added 17 parts stearic acid to form the vitamin and non-ferrous mineral blend. Approximately 749 grams of this blend is used to form the outer layer of the dietary supplement composition tablet, surrounding the ferrous core component prepared above by compression molding in a die to produce a tablet having a total weight of approximately 952 mg. The tablet is film coated with a commercial film coating agent, Opadry ® clear formulation by Colorcon, 2.3 parts, dissolved in a methanol/methylene chloride solvent containing 28.3 parts methanol to 47 parts methylene chloride and the solvent removed by drying to form the finished tablets having a weight of about 954 mg.

What is claimed is:

1. A multimineral dietary supplement composition for oral administration containing, per unit dose,
   (a) an outer layer having one or more divalent dietary mineral components selected from the group consisting of bioavailable calcium and magnesium, and in the further presence or absence of one or more additional non-ferrous mineral and vitamin components, adapted to be released in the upper gastrointestinal tract, and therein
   (b) a bioavailable iron core component iron free, present in controlled release form, so adapted so as to be subsequently released in a controlled manner lower in the gastrointestinal tract.

2. A multimineral composition according to claim 1, wherein the formulation is in the form of a tablet.

3. A multimineral composition according to claim 1, wherein said tablet also contains a protective film coating surrounding said outer layer of component (b).

4. A multimineral composition according to claim 2, wherein component (b) contains between about 15 and about 60 mg bioavailable iron.

5. A multimineral composition according to claim 4 wherein component (a) contains between about 50 and about 200 mg bioavailable calcium.

6. A multimineral composition according to claim 5, wherein component (a) also contains between about 5 and about 50 mg bioavailable magnesium.

7. A multimineral composition according to claim 4, wherein the bioavailable iron is in the form of ferrous sulfate.

8. A multimineral composition according to claim 5, wherein the bioavailable calcium is in the form of calcium carbonate or calcium sulfate.

9. A multimineral composition according to claim 6, wherein the bioavailable magnesium is in the form of magnesium oxide, magnesium hydroxide or magnesium sulfate.

10. A multimineral composition according to claim 1, wherein the inner core (b) contains the bioavailable iron component as a ferrous salt dispersed in a plastic or waxy matrix.

11. A multimineral composition according to claim 10, wherein the plastic or waxy matrix comprises a cellulose ether or cellulose ester film former and a release rate modifying agent.

12. A multimineral composition according to claim 10 wherein the iron component is designed to be continuously released from the tablet core over a period of about 2 and about 8 hours in the gastrointestinal tract.

13. A method of preventing or treating iron deficiency in a patient in need of the same, comprising orally administering to said patient two unit doses of the multimineral composition according to claim 6.

* * * * *